(12) United States Patent
Corbett

(10) Patent No.: US 9,254,281 B2
(45) Date of Patent: Feb. 9, 2016

(54) COMPOSITION AND METHOD FOR THE TREATMENT OF NEURODEGENERATION

(75) Inventor: Adrian M. Corbett, Dayton, OH (US)

(73) Assignee: Wright State University, Dayton, OH (US)

( * ) Notice: Subject to any disclaimer, the term of this patent is extended or adjusted under 35 U.S.C. 154(b) by 190 days.

(21) Appl. No.: 13/610,113

(22) Filed: Sep. 11, 2012

(65) Prior Publication Data

US 2013/0065924 A1    Mar. 14, 2013

Related U.S. Application Data

(60) Provisional application No. 61/533,428, filed on Sep. 12, 2011.

(51) Int. Cl.
| | | |
|---|---|---|
| A01N 33/02 | (2006.01) |
| A61K 31/135 | (2006.01) |
| A01N 43/16 | (2006.01) |
| A61K 31/35 | (2006.01) |
| A01N 43/08 | (2006.01) |
| A61K 31/34 | (2006.01) |
| A61K 31/366 | (2006.01) |
| A61K 31/375 | (2006.01) |
| A61K 31/4525 | (2006.01) |
| A61K 31/138 | (2006.01) |

(52) U.S. Cl.
CPC ............ *A61K 31/366* (2013.01); *A61K 31/138* (2013.01); *A61K 31/375* (2013.01); *A61K 31/4525* (2013.01)

(58) Field of Classification Search
USPC .................................................. 514/649, 460
See application file for complete search history.

(56) References Cited

U.S. PATENT DOCUMENTS

2006/0165807 A1* 7/2006 Castan et al. ................. 424/490

OTHER PUBLICATIONS

Reagan-Shaw, S. et al.; Dose translation from animal to human studies revisited; The FASEB Journal; Mar. 2007; pp. 659-661; vol. 22.

* cited by examiner

*Primary Examiner* — Layla Soroush
(74) *Attorney, Agent, or Firm* — Dinsmore & Shohl LLP

(57) ABSTRACT

A composition and method for the treatment of neurodegeneration and brain-derived neurotrophic factor. The composition and method comprising providing fluoxetine, simvastatin, and optionally, an antioxidant.

2 Claims, 8 Drawing Sheets

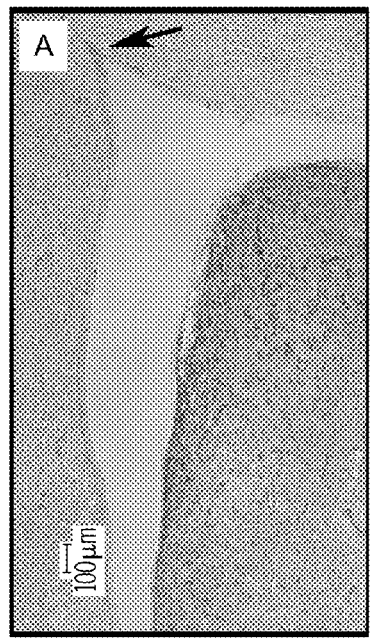 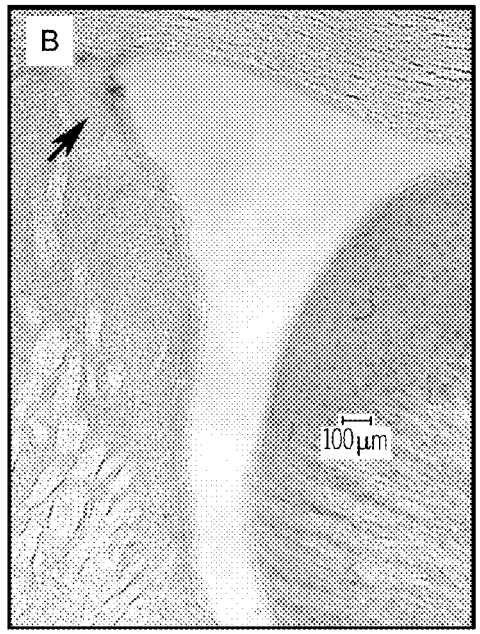
FIG. 1A  FIG. 1B
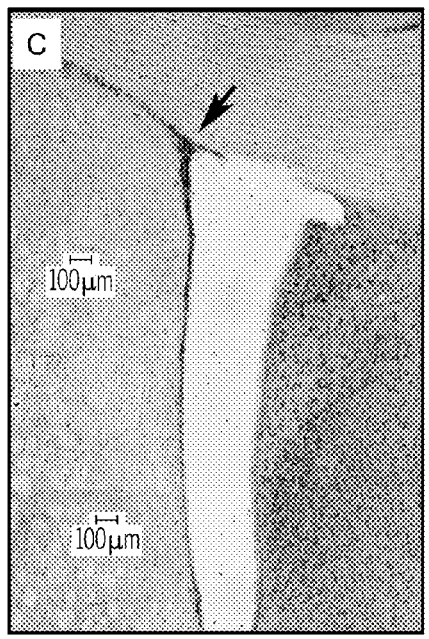 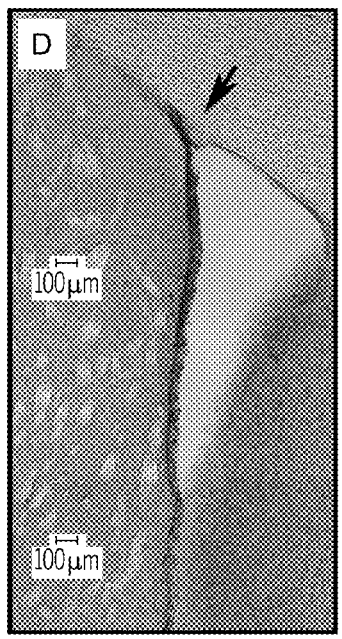
FIG. 1C  FIG. 1D

COMPOSITION AND METHOD FOR THE TREATMENT OF NEURODEGENERATION

CROSS-REFERENCE TO RELATED APPLICATIONS

This application claims the benefit of U.S. Provisional Application Ser. No. 61/533,428, filed on Sep. 12, 2011. The entire contents of that application are incorporated by reference herein.

FIELD OF THE INVENTION

The present invention relates to a composition and method for providing a delayed pharmacological treatment for brain injury, including ischemic stroke, using a combination of drugs to enhance neurogenesis and brain-derived neurotrophic factor.

BACKGROUND OF THE INVENTION

Stroke is one form of brain injury which is the primary cause of long term disability, with over 5 million stroke survivors in the United States and an associated cost of more than $50 billion in 2006 for care of ischemic (blood clot) stroke victims alone. The NHLBI's Framingham Study noted that in ischemic stroke survivors who were at least 65 years of age, the following disabilities were observed 6 months after the stroke: hemiparesis (50%); inability to walk without some assistance (30%); dependence in activities of daily living (26%); aphasia (19%); depressive symptoms (35%); and institutionalization in a nursing home (26%). The mean lifetime costs of ischemic stroke for an individual patient was estimated to be $140,048 in the United States, including inpatient care, rehabilitation and any follow-up care necessary for long-term deficits. Nationally, in 2006 only 3-8.5% of ischemic stroke patients received the clot buster drug (recombinant tissue plasminogen activator), which must be given in a short window of time after initiation of stroke. For more than 90% of ischemic stroke patients, there exists no standardized treatment in the days following the stroke other than giving aspirin.

Accordingly, there is a need in the art for effective therapies that minimize the damage from the event of brain injury, such as an ischemic stroke, or enhance the body's ability to recover from the adverse consequences of other forms of brain injury.

SUMMARY OF THE INVENTION

Embodiments of the present disclosure meet those needs by providing a composition and method for the treatment of neurodegeneration wherein functional recovery is achieved when the drug combination is administered between at least 20-26 hours after ischemic stroke induction and with continued daily administration for at least 31 days.

According to one aspect of the disclosure, a composition for the treatment of neurodegeneration is provided comprising fluoxetine, simvastatin, and optionally, an antioxidant.

According to another aspect of the disclosure, a composition is provided for the treatment of neurodegeneration comprising from about 5 mg/kg to 10 mg/kg by weight of fluoxetine, about 0.5 mg/kg to 2.6 mg/kg by weight of simvastatin, and optionally, 20 mg/kg by weight of an antioxidant in rats. Dose translation for humans is from about 0.81 mg/kg to 1.62 mg/kg fluoxetine, about 0.081 mg/kg to 0.42 mg/kg simvastatin, and 3.24 mg/kg of an antioxidant, corresponding to about 48.6 mg to 97.2 mg fluoxetine, about 4.86 mg to 25.2 mg simvastatin and 194.4 mg of an antioxidant for a 60 kg human.

According to another embodiment of the disclosure, a method for the treatment of neurodegeneration is provided comprising administering a composition comprising fluoxetine, simvastatin, and optionally, an antioxidant to a patient in need of such treatment.

According to a further embodiment of the disclosure, a method for the treatment of neurodegeneration comprising administering a composition comprising from about 5 mg/kg to 10 mg/kg by weight of fluoxetine, about 0.5 mg/kg to 2.6 mg/kg by weight of simvastatin, and optionally, 20 mg/kg by weight of an antioxidant in rats. Dose translation for humans is from about 0.81 mg/kg to 1.62 mg/kg fluoxetine, about 0.081 mg/kg to 0.42 mg/kg simvastatin, and 3.24 mg/kg of an antioxidant, corresponding to about 48.6 mg to 97.2 mg fluoxetine, about 4.86 mg to 25.2 mg simvastatin and 194.4 mg of an antioxidant for a 60 kg human.

According to a further embodiment of the disclosure, a composition for the treatment of neurodegeneration is provided comprising paroxetine, simvastatin, and optionally, an antioxidant.

According to another aspect of the disclosure, a composition is provided for the treatment of neurodegeneration comprising from about 5 mg/kg to 10 mg/kg by weight of paroxetine, about 0.5 mg/kg to 2.6 mg/kg by weight of simvastatin, and optionally, 20 mg/kg by weight of an antioxidant in rats. Dose translation for humans is from about 0.81 mg/kg to 1.62 mg/kg paroxetine, about 0.081 mg/kg to 0.42 mg/kg simvastatin, and 3.24 mg/kg of an antioxidant, corresponding to about 48.6 mg to 97.2 mg paroxetine, about 4.86 mg to 25.2 mg simvastatin and 194.4 mg of an antioxidant for a 60 kg human.

According to another embodiment of the disclosure, a method for the treatment of neurodegeneration is provided comprising administering a composition comprising paroxetine, simvastatin, and optionally, an antioxidant to a patient in need of such treatment.

According to a further embodiment of the disclosure, a method for the treatment of neurodegeneration comprising administering a composition comprising from about 5 mg/kg to 10 mg/kg by weight of paroxetine, about 0.5 mg/kg to 2.6 mg/kg by weight of simvastatin, and optionally, 20 mg/kg by weight of an antioxidant in rats. Dose translation for humans is from about 0.81 mg/kg to 1.62 mg/kg paroxetine, about 0.081 mg/kg to 0.42 mg/kg simvastatin, and 3.24 mg/kg of an antioxidant, corresponding to about 48.6 mg to 97.2 mg paroxetine, about 4.86 mg to 25.2 mg simvastatin and 194.4 mg of an antioxidant for a 60 kg human.

The method for dose translation from rats to humans is provided by Reagan-Shaw, S. et al., "Dose translation from animal to human studies revisited" FASEB J. 22: 659-661 (2007).

Accordingly, it is a feature of the present disclosure to provide a composition and method for the treatment of neurodegeneration. Other features and advantages of the invention will be apparent from the following description, the accompanying drawings, and the appended claims.

BRIEF DESCRIPTION OF THE DRAWINGS

The following detailed description of the illustrative embodiments of the present invention can be best understood when read in conjunction with the following drawings, where like structure is indicated with like reference numerals and in which:

FIGS. 1A-1E illustrate an effect on adult neurogenesis after treatment using a composition and method according to an embodiment of the present invention;

DETAILED DESCRIPTION

Figure 1E:
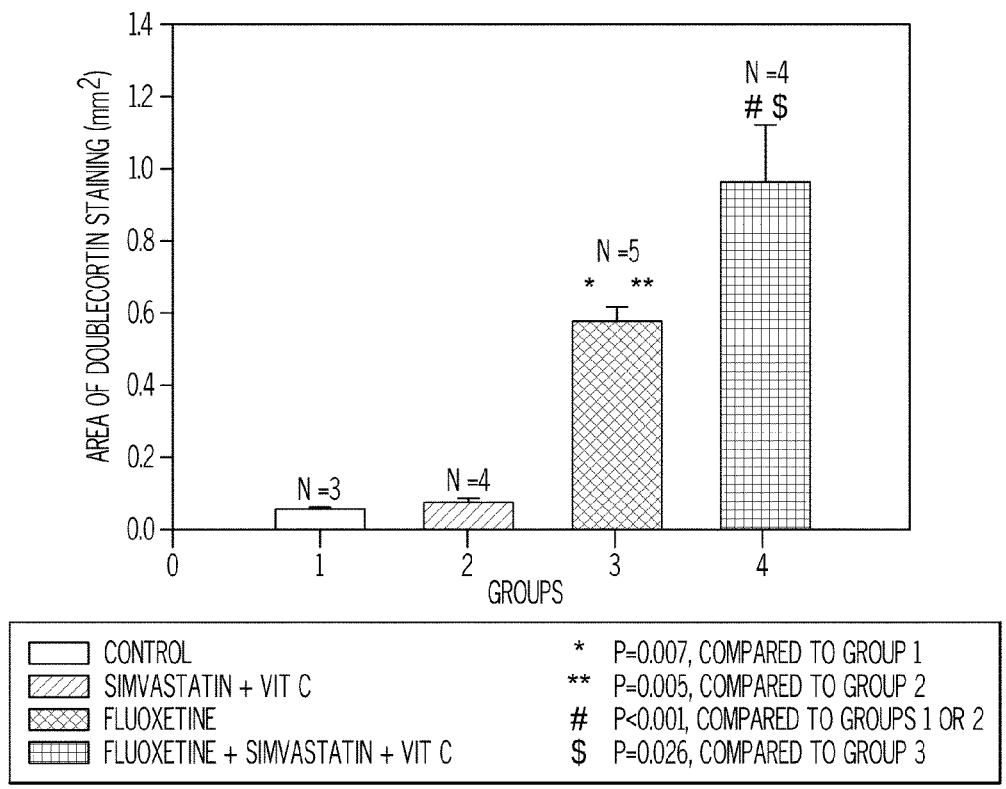

Embodiments of the present disclosure comprise a composition and method described herein which provide many advantages over prior treatments of neurodegeneration to minimize the damage from the event of brain injury such as an ischemic stroke or enhance the body's ability to recover from the adverse consequences of brain injury.

In one embodiment, the composition for the delayed post-stroke treatment comprises simvastatin and fluoxetine which are FDA-approved drugs that have been shown to increase neurogenesis and brain-derived neurotrophic factor (BDNF), which are believed to both increase neuronal survival and plasticity. Fluoxetine is a member of the selective serotonin reuptake inhibitors (SSRIs). Simvastatin is a member of the statin class of drugs. Ascorbic acid (vitamin C, an antioxidant) may be added to simvastatin and fluoxetine because serotonin is very sensitive to oxidation. An antioxidant has been found to enhance the effect of antidepressants (selective serotonin reuptake inhibitors), and statins work to increase brain derived neurotrophic factor through stimulation of endothelial nitric oxide synthase. Endothelial nitric oxide synthase has a component that is very sensitive to oxidation, and ascorbic acid has been shown to enhance activation of this enzyme.

The combination of fluoxetine, simvastatin, and ascorbic acid results in almost complete functional recovery when given up to 26 hours after ischemic stroke induction.

Fluoxetine, as well as fluoxetine in combination with simvastatin and ascorbic acid, produces a significant increase in neurogenesis as measured with doublecortin expression (10 fold and 19 fold compared to control) in the anterior subventricular zone of the lateral ventricles. Previous studies on fluoxetine's effect on neurogenesis used Bromodeoxyuridine (BrdU) to measure neurogenesis and generally only examined the subventricular zone in same slices with the dentate gyrus, which was more caudal and failed to show an effect of fluoxetine on neurogenesis.

As described herein, the combination of fluoxetine, simvastatin and ascorbic acid, first given 20-26 hours after ischemic stroke induction, results in recovery to 85-90% of pre-stroke motor function with functional tests that used either voluntary exploration or skilled grasping, with daily combination drug treatment for 31 days. However, it is noted that one side effect is the functional deficit in skilled grasping seen in the ipsilateral paw at post-stroke day 9, but fully recovered by the end of the 31 day treatment. This drug induced functional deficit is dependent on the statin, as removal of the statin in a composition comprising fluoxetine and ascorbic acid resulted in no ipsilateral paw deficit. This ipsilateral effect was never seen in Sprague Dawley rats, so it may be limited to the Long Evans rat strain. While not wishing to be bound by theory, it is believed that there are unique aspects with enhanced neurogenesis seen in the composition comprising fluoxetine, simvastatin, and ascorbic acid, with enhanced BDNF expression. The BDNF expression is known to increase synaptogenesis and may be involved in cortical rewiring for fine motor control. Once rewiring is achieved the function would return. Alternatively, it is possible that the statin caused some stiffness of the skeletal muscle. Rhabdomyolysis is a known side effect of statins, and sometimes certain statins given in combination with antidepressants cause this effect. However, if the ipsilateral functional deficit at post-stroke day 9 was caused by rhabdomyolysis, then the functional improvement by post-stroke day 30 should not have been seen.

Data suggests that drug treatments using three different compounds comprising fluoxetine, simvastatin, and ascorbic acid, or fluoxetine and ascorbic acid reduce the infarct size. The healed over appearance of the infarct in the composition comprising fluoxetine, simvastatin, and ascorbic acid was in contrast to the composition comprising fluoxetine and ascorbic acid and control in animals. It was observed that migrating neuroblasts approach the infarct in the composition comprising fluoxetine and ascorbic acid. The lack of migration in the control sections may be key to lack of functional recovery. The compositions comprising fluoxetine, simvastatin, and ascorbic acid did not show migrating neuroblasts to the infarct. This may have been because the infarct was already healed over by post-stroke day 32. Quantification of the infarct volume was performed in Sprage Dawley rats, in two different trials. Using either the original drug combination (fluoxetine, simvastatin, ascorbic acid) or different drug combinations (fluoxetine and simvastatin; paroxetine, simvastatin and ascorbic acid), a strong trend towards infarct volume reduction was observed, with P values just over the level for a significant difference. Paroxetine is another member of the SSRI class of drugs, testing whether a substitution of fluoxetine with another SSRI class member would be equally effective.

Figure 4A:
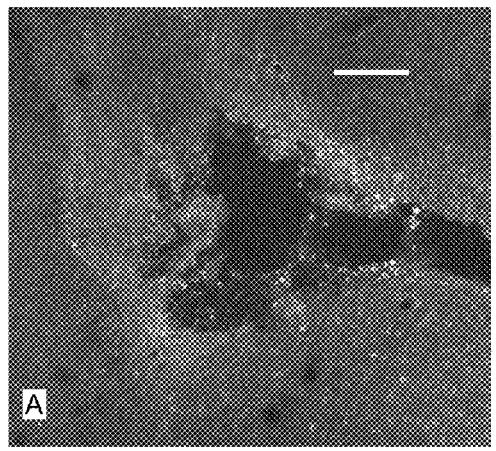
FIGS. 4A-4C illustrate doublecortin and BDNF expression near infarct according to an embodiment of the present invention.

BDNF production after ischemic stroke in rats has been evaluated in other laboratories, demonstrating that BDNF expression is only elevated for a very limited period of time, specifically, 8 days or less, following a stroke. FIG. 4A shows that an intermediate recovery drug treatment of fluoxetine combined with ascorbic acid elevated BDNF expression near the infarct 32 days following stroke induction. Fluoxetine is known to cause an increase in BDNF, whereas ascorbic acid has not been shown to directly increase BDNF, suggesting that fluoxetine is mediating the increase in BDNF expression.

In one embodiment, the composition comprises two well characterized FDA approved drugs, and the drugs given separately have shown some functional improvement post-stroke in clinical trials. While not wishing to be bound by theory, the results in the rat model may translate well to the human ischemic stroke population.

In order that the invention may be more readily understood, reference is made to the following examples which are intended to illustrate embodiments of the invention, but not limit the scope thereof.

In the following examples the experimental design and animals used were three strains of rats: male Wistar rats (10-12 months in age), female Long Evans outbred rats (10-12 months in age) and female Sprague Dawley outbred rats (10-12 months in age). The rats were housed under 12-hour light/12-hour dark conditions with ad libitum access to food and water outside of training or testing for Montoya staircase, where food was restricted.

Voluntary oral drug administration of generic or brand name pharmaceutical drugs comprising an 80 mg tablet of simvastatin, 20 mg capsule of fluoxetine HCl were used, and the weights of active ingredients were compared to total dry drug weights to account for any fill compounds. The correction factors for fill compounds comprising 10× for simvastatin and 7.5× for fluoxetine HCl were used to measure out the correct amount of active ingredients for each animal. Ascorbic acid (Vitamin C, Fluka) was used in pure form.

A vehicle control was used consisting of 4 grams of purchased sugar cookie dough, specifically Pillsbury. The cookie dough was weighed, rounded into a ball and then a depression pushed into the ball with a finger. The individually weighed drugs were put into the depression in the dough ball and rim edges of the depression were brought together and sealed so that all the dry chemicals were enclosed in the dough ball. The dough ball was thoroughly mixed manually to incorporate all of the chemicals into the dough, and reformed into a ball. Each ball either contained no drugs, vehicle control only, or the designated dosages of the drug compositions for each animal assigned to the different drug groups. The dough balls were presented to individually housed rats in a glass petri dish around noon each day and left in the cage until the next day. The majority of animals consumed their dough ball within 10 minutes, but some animals took a longer period of time. Any remaining dough ball found the next day was counted against the complete ingestion of the drug composition or vehicle for reliability of the voluntary oral administration.

The first drug composition comprised a combination of 0.5 mg/kg simvastatin and 20 mg/kg ascorbic acid. The second drug composition comprised 5 mg/kg fluoxetine. The third drug composition comprised a combination of 0.5 mg/kg simvastatin, 5 mg/kg fluoxetine and 20 mg/kg ascorbic acid.

Example 1

The following is the procedure used to determine an effect on adult neurogenesis after treatment as described in the following experiment, wherein test results are illustrated in FIGS. 1A-1E.

Animals, more specifically, male Wistar rats were used to measure differences in neurogenesis in the subventricular zone of the lateral brain ventricles in response to the various drug treatments using doublecortin primary antibody to measure neurogenesis.

The male Wistar rats aged approximately one year old were used, wherein a doublecortin antibody was used to measure neurogenesis with a horseradish peroxidase labeled secondary antibody developed with 3,3'-Diaminobenzidine (DAB).

Three drug compositions, simvastatin and ascorbic acid; fluoxetine; and fluoxetine, simvastatin and ascorbic acid, were tested against vehicle control for their effect on neurogenesis in the subventricular zone of the anterior lateral ventricles. Wherein, the male Wistar rats were given voluntary oral drug treatments daily for a two week period.

A few animals in each group were euthanized and the brain dissected for immunofluorescence, for measurement of either neurogenesis or neurogenesis and BDNF expression. For example, four groups of Wistar rats, n=6 in each, were given a vehicle control or one of three drug compositions which are voluntary orally administered for a period of two weeks, euthanized and the brain dissected for immunohistochemistry.

Specifically, all dissected animal brains were blocked and post fixed for 24 hours in 4% paraformaldehyde in PBS at 5° C. The brains were then put into 30% sucrose in PBS at 5° C. for at least 3 days and then cut on a cryostat into 50 micron coronal sections. The sections were collected into PBS, blocked for one hour with PBS containing 1% Tween and 3% secondary antibody host serum, then reacted with doublecortin primary antibody, 1:500 dilution in blocking solution. The Wistar rats used Abcam antibody and the Long Evans rats used Cell Signaling antibody for at least 16 hours at 5° C. If BDNF antibody, Millipore, was also used, then incubation lasted 72 hours at 5° C. at a 1:250 dilution in blocking solution. Free-floating sections were washed with 3 washes of PBS containing 0.1% Tween, then incubated in the dark with secondary antibodies, Cy3-labeled Donkey anti-rabbit IgG, FITC-labeled Donkey anti-sheep IgG; Jackson Immunology, at a 1:100 dilution in blocking solution for 2.5 hours at room temperature or a Vector ABC elite horseradish peroxidase DAB kit was used according to kit instructions, mounting the final washed sections on gel-subbed slides. Sections with fluorescent secondary antibodies were washed three times with PBS containing 0.1% Tween and then the sections were mounted on gel-subbed slides.

As shown in FIGS. 1A-1D, neurogenesis was examined using doublecortin primary antibody and peroxidase labeled secondary antibody to label migrating neuroblasts arising from the subventricular zone of the lateral ventricles in free floating 50 micron coronal slices. Wherein a representative subventricular zone (left side of the lateral ventricle) from animals receiving daily doses of A: vehicle only (Control); B: 0.5 mg/kg simvastatin and 20 mg/kg ascorbic acid; C: 5 mg/kg fluoxetine; or D: 5 mg/kg fluoxetine, 0.5 mg/kg simvastatin, and 20 mg/kg ascorbic acid. The Area of doublecortin staining was quantified using NIH's software for image analysis (Image J) and shown in FIG. 1E. ANOVA (analysis of variance) was used for statistical analysis.

Results

Control neurogenesis, shown in FIG. 1A, near the indicated arrow, and quantified in FIG. 1E, Group 1: mean of 0.0508 mm$^2$. Simvastatin and ascorbic acid did not produce an increase in neurogenesis different from vehicle control, see FIG. 1B; quantified in Group 2 of FIG. 1E: mean of 0.0719 mm$^2$. However, fluoxetine caused a significant increase in neurogenesis, P=0.007 compared to vehicle control; P=0.005 compared to simvastatin plus ascorbic acid, see FIG. 1C; dark staining along left side of ventricle, indicated by arrow; quantified in Group 3 of FIG. 1E: mean of 0.5727 mm$^2$. The mean increase in neurogenesis was approximately 10 fold greater than vehicle control. Fluoxetine in combination with simvastatin and ascorbic acid produced approximately a 19 fold increase in neurogenesis, see FIG. 1D; quantified as Group 4 in FIG. 1E: 0.9675 mm$^2$ over vehicle control, which is significantly different from either vehicle control or simvastatin plus ascorbic acid groups, P<0.001, as well as the fluoxetine group, P=0.026. Thus, as shown in FIGS. 1A-1E, the area of doublecortin staining, evidencing neurogenesis, was greatest for animals receiving the combination of fluoxetine, simvastatin, and ascorbic acid.

Example 2

Figure 2A:
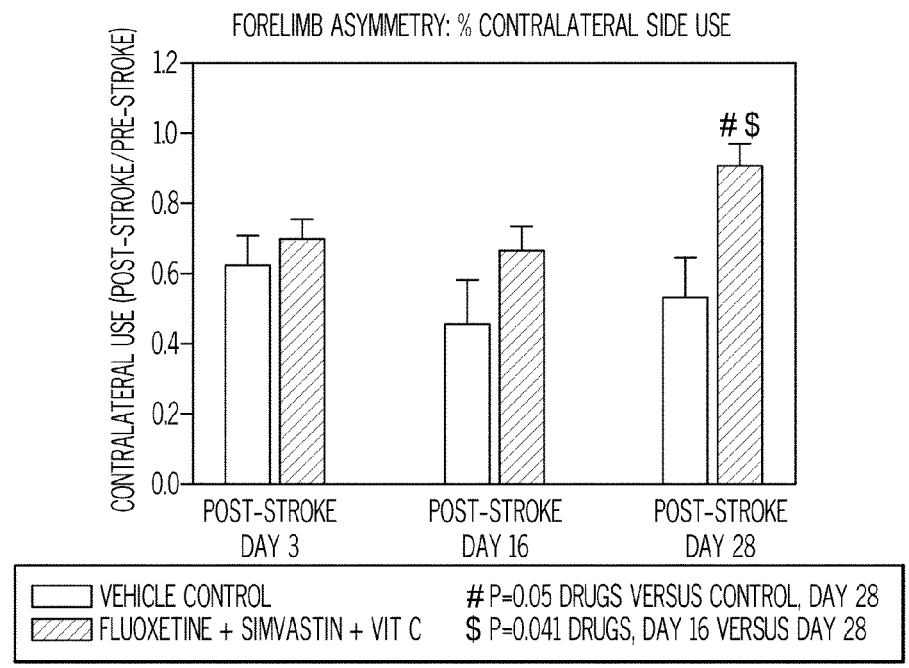
FIGS. 2A-2C illustrate forelimb asymmetry tests according to an embodiment of the present invention.
Figure 2B:
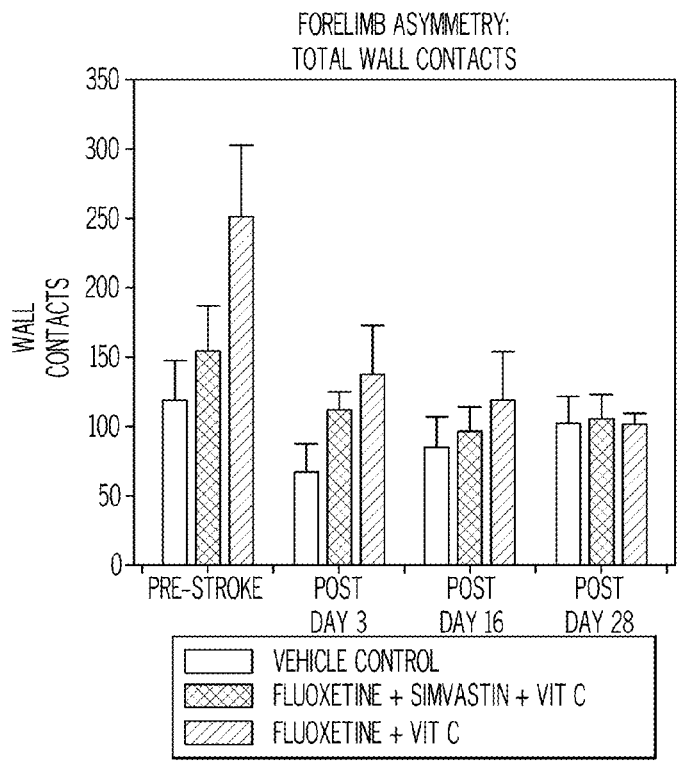
Figure 2C:
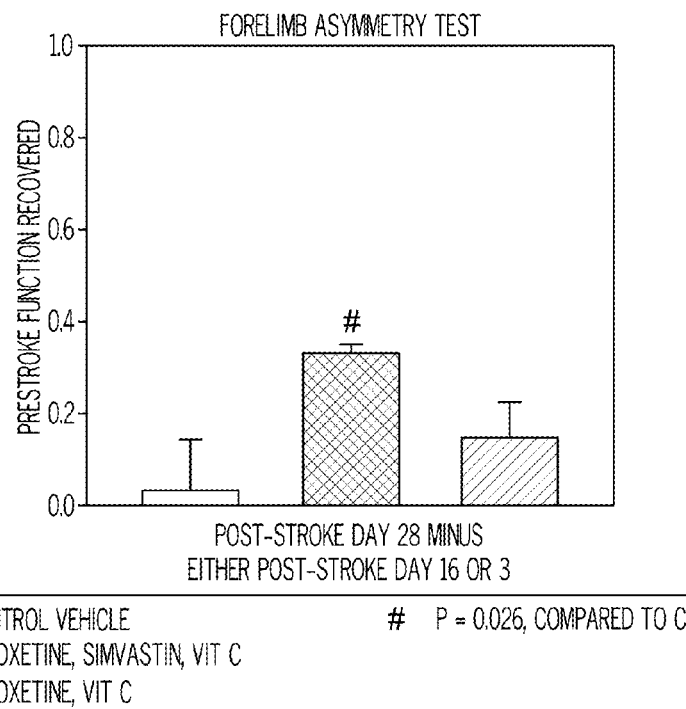

The following is the procedure used in the forelimb asymmetry tests as described in the following experiment, wherein test results are illustrated in FIGS. 2A-2C.

Animals, more specifically, three groups of Long Evans female retired breeder rats, approximately 1 year old, n=11 each, were tested in forelimb asymmetry, then subjected to endothelin-induced cortical stroke.

The animal groups were given either vehicle control or one of two drug combinations, fluoxetine and ascorbic acid; and fluoxetine, simvastatin and ascorbic acid, beginning 20-26 hours after stroke induction and continued daily voluntary oral administration for a period of 31 days. The animals were tested for functional recovery using the forelimb asymmetry tests on post-stroke days 3, 16 and 28.

The forelimb asymmetry test was used to evaluate post-stroke functional recovery through comparison with pre-stroke function. The forelimb asymmetry test video recorded the animal's voluntary exploratory behavior in a clear vertical cylinder, quantifying the number of wall contacts by either right or left forepaw. Specifically, the animals were placed in a clear acrylic 9 inch inner diameter vertical tube on a stand with maple extract painted approximately 14 inches from the bottom and video recorded for 5 minutes. The video recordings were analyzed in slow motion, counting the number of wall contacts made with the right forepaw and the left forepaw.

All animals received an endothelin-induced cortical stroke in the right hemisphere as described in Example 4. All animals received vehicle on the day of stroke surgery and the daily medicine was given 20-26 hours after stroke induction and continued for 31 days. N=6 in vehicle control and N=7 for Fluoxetine Combo (5 mg/kg fluoxetine, 0.5 mg/kg simvastatin, 20 mg/kg ascorbic acid) groups.

With regards to the female Long Evans rats that were subjected to surgery to produce a small cortical stroke using endothelin injections in two adjacent brain locations, a typical infarct size in control animals was found to average 8.35±3.31 (SD) $mm^3$ at 32 days post-stroke using Nissl stain (N=6) in Long Evans rats using the method of stroke induction determined in an experiment used in functional recovery described in Example 4.

Results

Following stroke induction in the right hemisphere of the brain, the animals displayed a decrease in the left forepaw, contralateral, contacts with the wall; see FIG. 2A, which lasts in control animals over the test period of 28 days with little recovery. The percentage of contralateral contacts with the wall for each post-stroke time period for an individual rat is divided by the pre-stroke percentage of contralateral contacts.

As shown in FIG. 2A, the post-stroke percentage of left forelimb contacts/pre-stroke percentage of left forelimb contacts for post-stroke days 3, 16 and 28. If animals fully recovered from stroke, then this quotient would be 1; any number less than 1 shows a functional deficit in that forepaw. For example, a value of 0.6 indicates the animal has 60% of its pre-stroke function or a functional deficit of 40%. The fluoxetine, simvastatin and ascorbic acid daily treatment which began 20-26 hours after stroke induction resulted in almost complete recovery at post-stroke day 28 with 95% of its pre-stroke function which is significantly different from control at post-stroke Day 28. Repeated measures ANOVA indicated a P=0.05 for Fluoxetine Combo versus control on Day 28 and a P=0.041 for Fluoxetine Combo comparing Day 16 and Day 28 (Tukey post-hoc test).

As shown in FIG. 2B, the total number of wall contacts made for each group at the four time points with the two drug groups versus control. Repeated measures ANOVA indicated that the only significant difference (P<0.001) was for pre-stroke values compared to post-stroke values, thus, there was no significant difference between the two drug groups. Thus there is no overall difference in exploration behavior with the drug treatments, just the paws (contralateral versus ipsilateral) that are used to explore the wall.

FIG. 2C illustrates the test results of the effect of either vehicle control (N=6), the fluoxetine combo (N=7), or fluoxetine plus Vitamin C (N=3) on contralateral limb functional recovery. The functional recovery was quantified over the test period using post-stroke values at Day 28 minus the lowest value of post-stroke function, from either Day 3 or Day 16, for two drug groups versus control. Control animals only experienced a mean recovery of 3.4% of their pre-stroke function, compared to 32.8% of pre-stroke function recovered for the 3-drug combination (fluoxetine, simvastatin and ascorbic acid) and 14.7% of pre-stroke function recovered using a combination of fluoxetine and ascorbic acid. A t-test was used to compare the post-stroke recovery using the composition of fluoxetine, simvastatin and ascorbic acid compared to control, which resulted in a significant difference, P=0.026. Removal of the simvastatin in the two drug combination (fluoxetine and ascorbic acid) approximately halved the functional recovery, indicating that the simvastatin is an essential component for full recovery. Fluoxetine is likely to be the other essential component, as a recent clinical trial showed similar levels of functional recovery following delayed administration following ischemic stroke.

Example 3

The following is the procedure used in the Montoya staircase tests as described in the following experiment, wherein test results are illustrated in FIGS. 3A-3D.

Animals, more specifically, three groups of Long Evans rats, n=11 each, were trained for Montoya staircase retrieval of sucrose pellets for two weeks, then subjected to endothelin-induced cortical stroke.

The animal groups were given either vehicle control or one of three drug combinations beginning 20-26 hours after stroke induction and continued daily voluntary oral administration for a period of 31 days. The animals were tested for functional recovery using the Montoya staircase tests on post-stroke days 8-10 and 29-31.

Prior to beginning training on the Montoya staircase, animals were fasted overnight. During the training animals received restricted rat chow, equivalent to 85% of their ad lib feed/day. Training took place during the dark phase, with one 15 minute test each day for each rat for a maximum of two weeks. Each well of the staircase contained three 50 mg sucrose pellets, which had been painted with maple extract and allowed to completely dry. The final three days of training were used to establish the pre-stroke baseline, with the best performance used, specifically, the total number of pellets retrieved. If more than one trial had the same number of total pellets retrieved for the best performance, but different performance for the forelimbs, then the results were averaged. Animal weight was not allowed to fall below 90% of their ad lib feeding weight during training. Post-stroke tests followed an initial overnight fast and testing for three days in the dark phase. Animal rat chow and the vehicle control, sugar cookie dough ball, for this time period totaled 10 grams per day. Any pellets the animal retrieved were not counted against their total food in either the training or post-stroke testing. Only animals retrieving at least 9 pellets in each forepaw by the end of training were included in this part of the functional analysis. Those animals failing to retrieve any pellets during post-stroke tests were excluded from this part of the functional analysis.

Stroked animals were tested for recovery using the Montoya staircase, a test of skilled grasping and retention of sucrose pellets, which separates left and right forepaw function. The number of sucrose pellets retrieved at different times post-stroke was divided by the pre-stroke baseline retrieval of pellets to normalize recovery and functional deficits for all animals.

Post stroke drugs tested (administered beginning 20-26 hours after stroke, and daily for 31 days) were vehicle control (N=4), 5 mg/kg fluoxetine+0.5 mg/kg simvastatin+20 mg/kg ascorbic acid (vitamin C), (N=4) or 5 mg/kg fluoxetine+20 mg/kg ascorbic acid. (N=3).

Results

The composition of fluoxetine, simvastatin and ascorbic acid was tested against control, beginning at post-stroke Day 8-10 and finally at post-stroke day 29-31. For simplicity, the best performance, total number of pellets retrieved, during both of these separate three day trials was denoted post-stroke Day 9 or post-stroke Day 30, see FIGS. 3A and 3B.

Figure 3A:
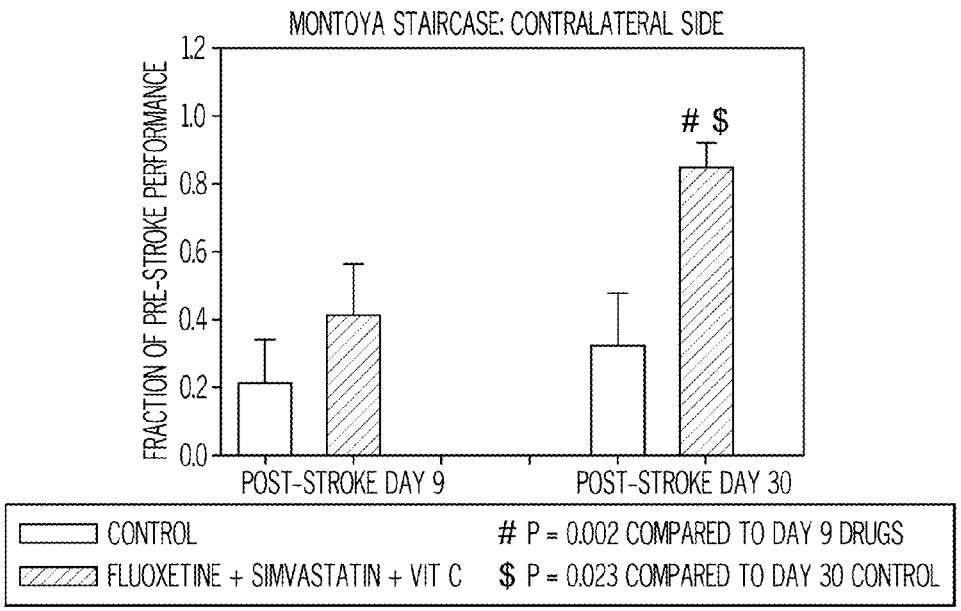
FIGS. 3A-3D illustrate Montoya staircase tests according to an embodiment of the present invention.

FIG. 3A examines contralateral limb function post-stroke, which should be impaired, wherein Y-axis values were determined. The functional deficit in this functional test is greater than that seen in the forelimb asymmetry test, as this test requires finer motor control. Wherein the test achieved an average functional deficit of 70% of pre-stroke function which was lasting over the 31 day test period in the control animals, but like the forelimb asymmetry test, little recovery in control animals was observed. At post-stroke day 30 the composition of fluoxetine, simvastatin and ascorbic acid produced a significant recovery of function, (P=0.023) mean of 85% of pre-stroke function was obtained, compared to control at this time point. Data was analyzed with repeated measures ANOVA, with P values shown in FIG. 3A.

Figure 3B:
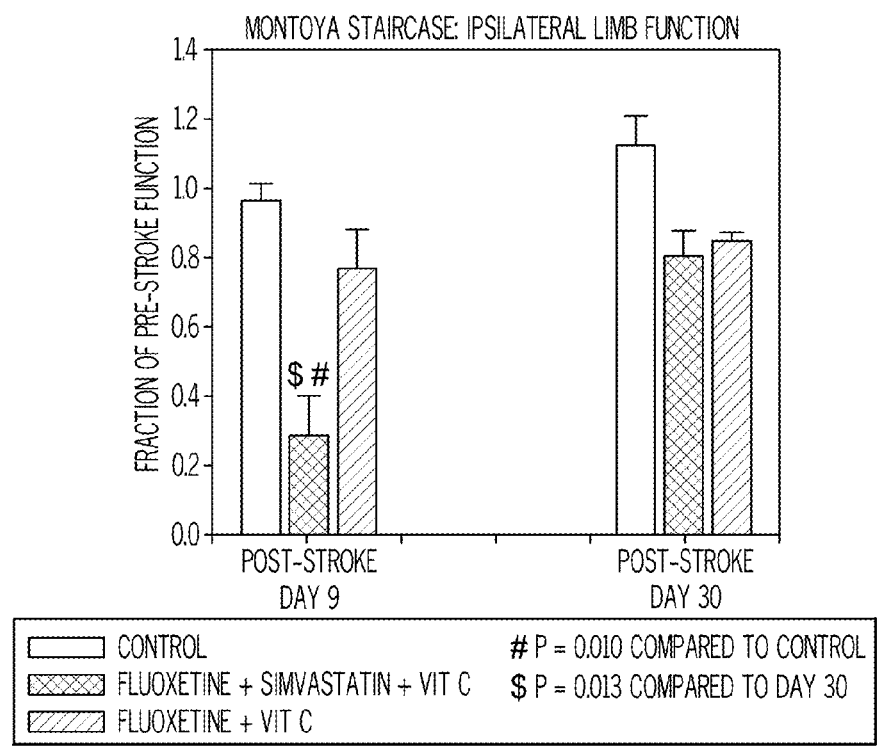

Ipsilateral function which is evaluated using two different compositions, fluoxetine, simvastatin and ascorbic acid; and fluoxetine and ascorbic acid compared to control as illustrated in FIG. 3B. The number of pellets retrieved in each limb at indicated post-stroke day, highest total number of pellets retrieved in 3-day test period, was divided by the number of pellets retrieved in the pre-stroke period, highest total number of pellets retrieved in final 3 days of training. Ipsilateral limb should not generally be affected by an ipsilateral stroke, but the results show that the 3-drug combination, fluoxetine, simvastatin and ascorbic acid, produces a deficit in ipsilateral function that is recovered almost completely by post-stroke day 30. As can be seen in FIG. 3B, any impairment of ipsilateral function due to the stroke, shown with control and the drug composition fluoxetine and ascorbic acid, but the composition of fluoxetine, simvastatin and ascorbic acid produces a significant functional deficit, (P=0.010), at post-stroke Day 9. This effect appears to be related to the presence of the statin, since the removal of simvastatin in the fluoxetine and ascorbic acid composition allows normal function in the ipsilateral limb. Function in this limb is restored by post-stroke Day 30, P=0.013, giving similar function to the composition of fluoxetine and ascorbic acid. The control animals displayed better ipsilateral function at post-stroke Day 30, in compensation for the loss of function in their contralateral limb. Data was analyzed with repeated measures ANOVA, with P values shown in FIG. 3B.

Figure 3C:
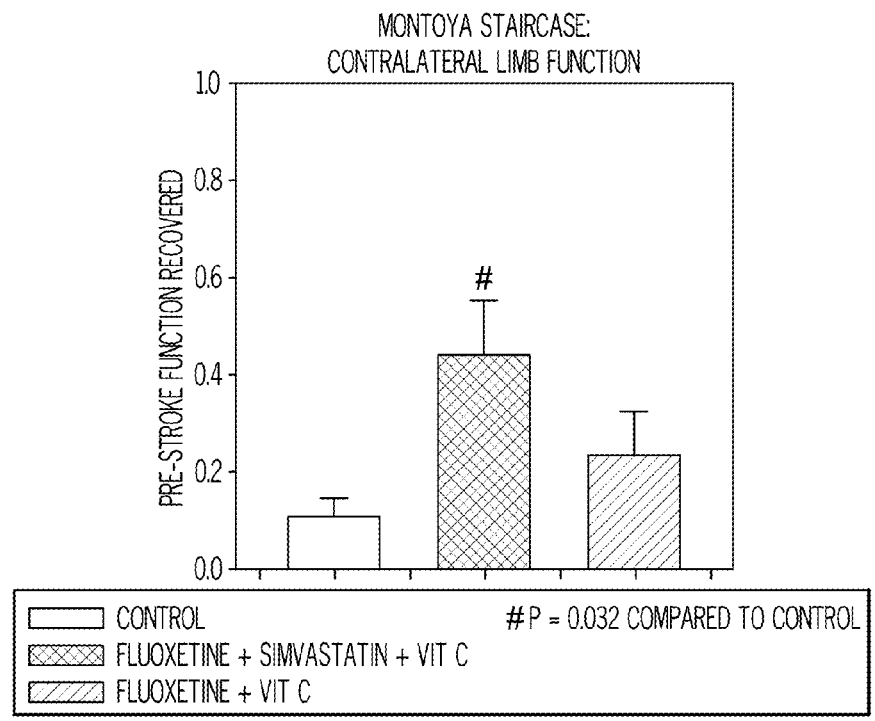

The amount of pre-stroke function recovered, function at post-stroke day 30 minus post-stroke day 9, is evaluated for the two different drug compositions and control as shown in FIG. 3C. Control animals had a mean 10.86% recovery of pre-stroke function over the 31 day period of treatment, whereas the composition of fluoxetine, simvastatin and ascorbic acid showed a mean 43.91% recovery and the composition of fluoxetine and ascorbic acid showed a mean 23.63% recovery. The recovery using the composition of fluoxetine, simvastatin and ascorbic acid was significantly different from control using a T-test, P=0.032. This recovery trend for the two drug groups versus control is again similar to that seen with the forelimb asymmetry test, with the composition of fluoxetine and ascorbic acid having about a 12% increase in recovery over control and the composition of fluoxetine, simvastatin and ascorbic acid showing more than a doubling of that recovery, 32.9% recovery over control.

Figure 3D:
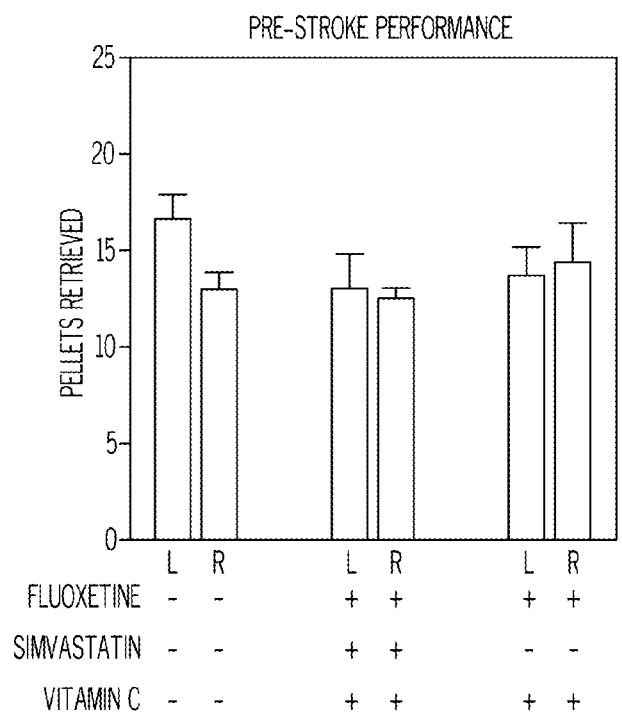

Finally, FIG. 3D examines pre-stroke baseline training for each drug composition, showing the number of pellets retrieved in each forepaw at the end of training for each drug group thus resulting in no significant differences between function in either between groups (Two Way ANOVA, P=0.338).

Example 4

Figure 4B:
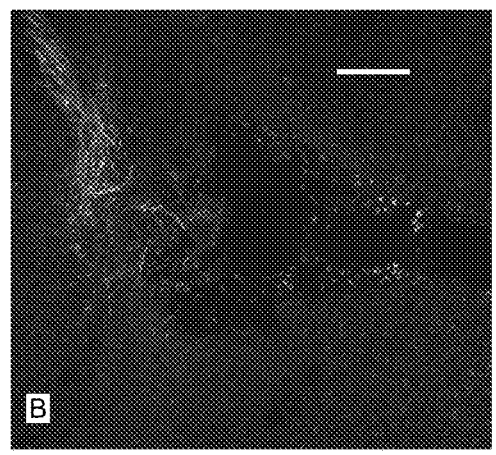
Figure 4C:
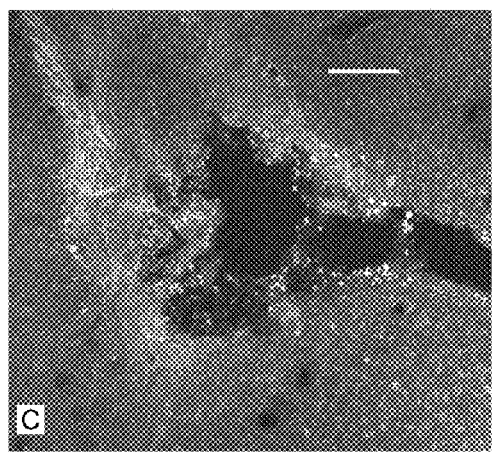

The following is the procedure used in the doublecortin and BDNF expression near infarct as described in the following experiment, wherein test results are illustrated in FIGS. 4A-4C.

Animals, more specifically, Wistar rats (10-12 months in age) and Long Evans rats (10-12 month), which were previously trained on the aforementioned Montoya staircase and forelimb asymmetry tests. Combination drug treatments comprising fluoxetine and ascorbic acid were tested against vehicle controls, beginning 20-26 hours after endothelin-induced stroke and continuing for 31 days. Functional tests were performed at various times post-stroke.

The endothelin-induced stroke consisted of anesthesia being induced by inhalation of 5% isoflurane. The head was shaved, Puralube™ ointment administered to the rodent's eyes, and the animal mounted in a stereotactic apparatus using non-traumatic ear bars. Anesthesia was maintained with 2-2.5% isoflurane inhalation during surgery. The surgical site was cleaned first with provoiodine, then 70% ethanol, and finally provoiodine and a midline incision was made on the top of the head. 0.25% bupivicaine was administered to the incision in several drops. A micro-drill (Fine Science Tools), with a 0.9 mm burr drill, was used to drill two holes in the skull at AP: 0.0 mm, ML: −2.5 mm and AP +2.3 mm; ML: −2.5 mm. Endothelin 1 (Human and Porcine, EMD Chemicals) at a concentration of 400 pmoles/μl was injected into each site at a depth of 2.3 mm in a total volume of 1 μl (modified from the procedure of Windle et al.) over the time-course of 2 minutes. The incision was sutured with Vicryl resorbable sutures and painted with provoiodine. No post-operative analgesia, besides bupivicaine, was used, as all have been shown to modulate neurogenesis. All animals were given the drug vehicle control comprising 4 grams of purchased sugar cookie dough following surgery to help accustom them to the vehicle control.

The animals were injected intraperitoneal with 100 mg/kg pentobarbital (Euthasol) and were cardioperfused with at least 150 ml of PBS when the animals were in a surgical plane of anesthesia. The Wistar rats and some Long Evans rats were then cardioperfused with 4% paraformaldehyde in PBS if staining for doublecortin or Zamboni's fixative and some Long Evans rats were cardioperfused with 4% paraformaldehyde in PBS if staining for both doublecortin and BDNF.

Results

The results of the doublecortin and BDNF expression near infarct are illustrated in FIGS. 4A-4C. Results in 50 micron brain sections at the end of 31 day fluoxetine and ascorbic acid treatment of endothelin-induced stroke, stained with antibodies to brain derived neurotrophic factor, FIG. 4A, as well as doublecortin, FIG. 4B. Merged images are shown in FIG. 4C. Fluorescence is indicative of cells having both doublecortin and BDNF present. Scale bar equals 200 microns.

Specifically, FIG. 4A shows BDNF expression (FITC labeled secondary) around the area of the infarct, showing increased expression around much of the infarct and along the path traveled by the migrating neuroblasts in FIG. 4B. FIG. 4B shows doublecortin labeled neuroblasts (CY3 labeled secondary antibody), arising from the subventricular zone of the anterior lateral ventricles, migrating to the cortical infarct. FIG. 4C shows a merged confocal image of the two antibody labeling, with some overlapped labeling seen around the area of the neuroblasts near the infarct, suggesting some neuroblasts might be secreting BDNF or turning into some other type of cell (glia) that are capable of secreting BDNF. All cells were evaluated for evidence of autofluoresence, by checking other wavelengths, and only the large round cells near the edge of the infarct are due to autofluoresence.

Example 5

Figure 5A:
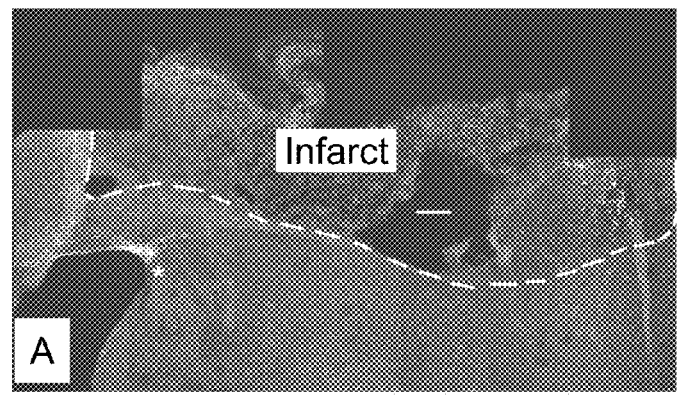
FIGS. 5A-5C illustrate an effect of treatments on infarct size and neuroblast migration according to an embodiment of the present invention.
Figure 5B:
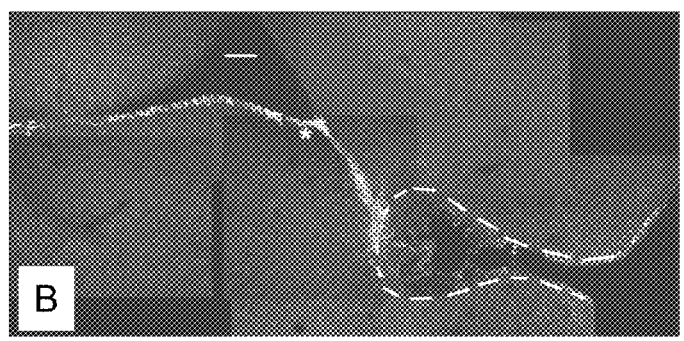
Figure 5C:
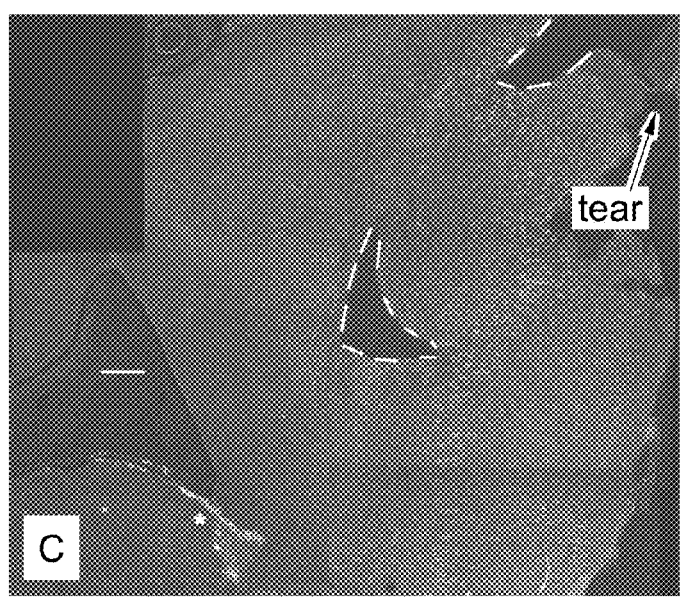

The following is the procedure used to illustrate an effect of treatments on infarct size and neuroblast migration in Long Evans rats, wherein the results are illustrated in FIGS. 5A-5C.

All brain section areas were imaged at 10× power, then, put together in a montage of the region. Arrows indicate doublecortin labeled neuroblasts at the subventricular zone of the right lateral ventricle. Areas outlined by dotted lines are regions of the infarct, found after 31 days of either vehicle control, see FIG. 5A; 5 mg/kg fluoxetine plus 20 mg/kg ascorbic acid, see FIG. 5B; or 5 mg/kg fluoxetine, 0.5 mg/kg simvastatin, plus 20 mg/kg ascorbic acid, see FIG. 5C. There were not sufficient brains analyzed in the control and fluoxetine, simvastatin and antioxidant drug combination groups for infarct volumes to quantify these results and test for statistical difference.

Results

FIGS. 5A-5C compares neuroblast migration and infarct size in the three different drug compositions. Results indicate that the infarct size is larger in the control animals and dramatically reduced in the drug composition of fluoxetine, simvastatin and ascorbic acid. While not wishing to be bound by theory, the infarct in the control animals did not appear to have many healed regions, tissue looks mangled, with many holes in tissue, however, observations did not show any neuroblasts migrating from the ventricles to the site of injury. Therefore, the infarct in the drug composition of fluoxetine, simvastatin and ascorbic acid shows to have clean edges, no mangled appearance in the center of the cortex, and does not show neuroblast migration. Thus, the fluoxetine and ascorbic acid combination produced an intermediate size infarct. One part of the infarct, near the cortical surface, healed over having smooth edges, while the infarct deeper in the cortex has rough edges and is attracting migrating neuroblasts. The area of the infarct with rough edges is also surrounded by increased BDNF expression, see FIG. 4A, which may be contributing to the healing process.

Example 6

Figure 6A:
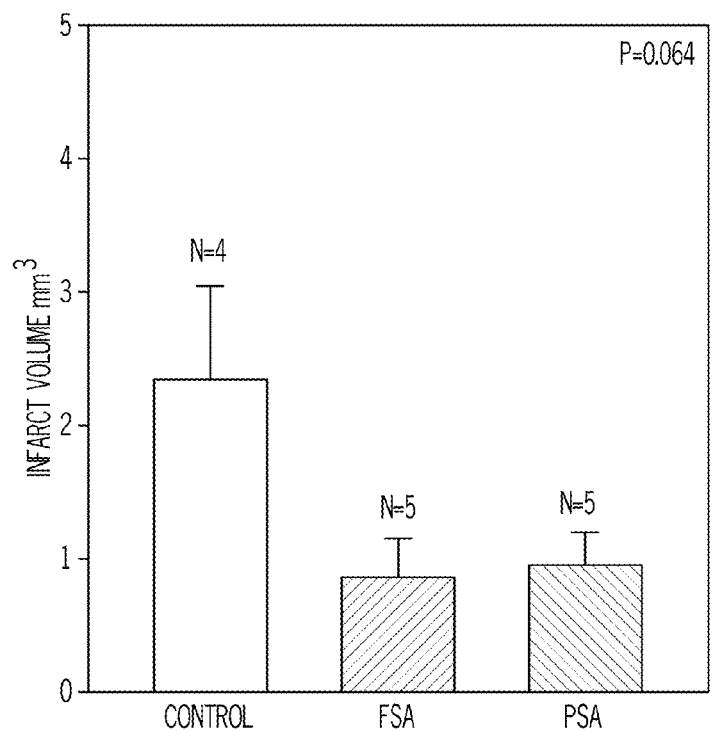
FIGS. 6A-6B illustrate an effect of treatments on infarct size according to an embodiment of the present invention.
Figure 6B:
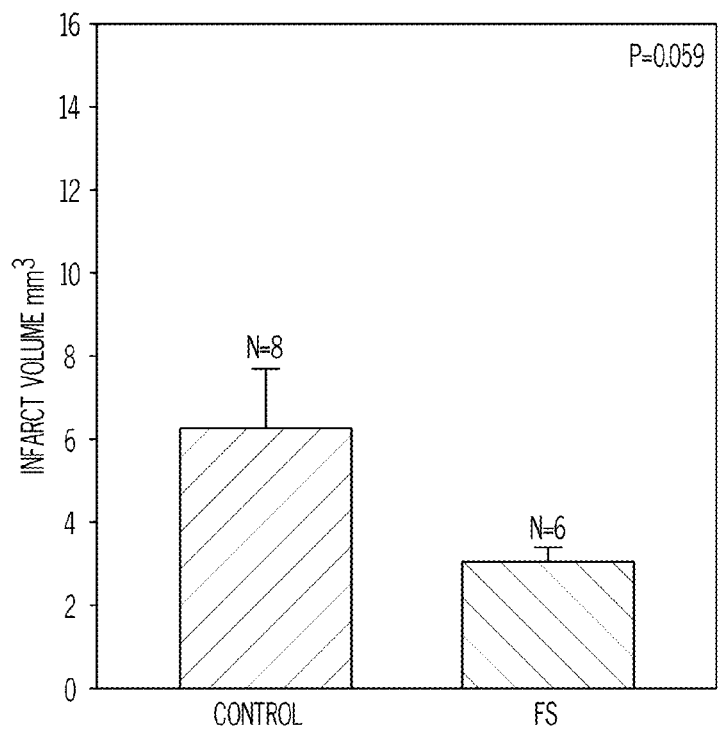

The following is the procedure used to illustrate an effect of treatments on infarct size in Sprague Dawley rats, wherein the results are illustrated in FIGS. 6A-6B.

All of the infarct area measurements were performed in Sprague Dawley rats (10-12 months in age) using either the same stereotactic coordinates as Long Evans rats, subjected to the same endothelin induced stroke and drug treatments or closer stereotactic coordinates combined with larger endothelin injections, using alternate injection coordinates and amount of injected endothelin producing infarcts that more closely resemble those produced in Long Evans rats. Two additional drug groups were added in these tests: PSA: (5 mg/kg paroxetine, 0.5 mg/kg simvastatin, and 20 mg/kg ascorbic acid) and FS: (5 mg/kg fluoxetine and 0.5 mg/kg simvastatin). Infarct regions were either assessed on a confocal fluorescent microscope or a brightfield scope, when sections were stained with cresyl violet stain, as illustrated in FIG. 6B.

Infarct volumes were quantified in FIGS. 6A-6B. Specifically, in FIG. 6A, infarcts were induced with 1 µl endothelin injections in each of two stereotactic coordinates (same coordinates as Long Evans rats). In FIG. 6B, infarcts were induced with 1.5 µl endothelin injections in each of two stereotactic coordinates: (AP 0.0 mm, ML −2.5 mm, DV 2.0 mm) and (AP 1.5 mm, ML −2.5 mm, DV 2.0 mm). In FIG. 6A, every third 50 micron coronal brain section was measured for infarct volume using Image J while in FIG. 6B, every fourth section was analyzed. Groups in FIGS. 6A and 6B were control, FSA (5 mg/kg fluoxetine, 0.5 mg/kg simvastatin, 20 mg/kg ascorbic acid), PSA (5 mg/kg paroxetine, 0.5 mg/kg simvastatin, 20 mg/kg ascorbic acid) and FS (5 mg/kg fluoxetine, 0.5 mg/kg simvastatin). Error bars represent Standard Error of the Mean (SEM). Statistical Normality tests (Shapiro-Wilk) failed, so Kruskal Wallis One Way Analysis of Variance on Ranks was performed in FIG. 6A, and Mann-Whitney Rank Sum test was performed in FIG. 6B with resulting P values shown in each FIGS. 6A and 6B.

Results

In both FIGS. 6A and 6B, a strong trend towards reduction in infarct volumes using either fluoxetine, simvastatin, ascorbic acid combination, FIG. 6A; or a fluoxetine and simvastatin combination, FIG. 6B, were shown suggesting that ascorbic acid is not an essential part of this drug combination. Paroxetine was evaluated in place of fluoxetine in the drug combination, wherein a strong trend towards reduction in infarct volume was shown, see FIG. 6A. If these drug combinations are able to affect infarct volumes given at this large delay (20-26 hours) after stroke induction, then one may hypothesize that giving the drug combination earlier would result in significant reductions in infarct volumes and better functional recovery.

The results of the experiments performed as described in the above examples indicate that daily treatments of 5 mg/kg fluoxetine in combination with 0.5 mg/kg simvastatin and 20 mg/kg ascorbic acid produced a 19-fold increase in neurogenesis, P=0.001, compared to vehicle control. This combination drug treatment resulted in almost complete functional recovery as measured by Montoya Staircase, mean recovery to 85% of pre-stroke function P=0.023; and Forelimb Asymmetry tests, mean recovery to 90% of pre-stroke function P=0.041 and P=0.05 in 10-12 month old stroked female rats. Additional testing of 5 mg/kg fluoxetine and 20 mg/kg ascorbic acid drug combination as a delayed post-stroke treatment resulted in half of the functional recovery opposed to the fluoxetine, simvastatin and ascorbic acid drug composition, therefore indicating that the statin is essential for full recovery. Further testing of the drug combinations FSA (5 mg/kg fluoxetine, 0.5 mg/kg simvastatin, 20 mg/kg ascorbic acid) and PSA (5 mg/kg paroxetine, 0.5 mg/kg simvastatin, 20 mg/kg ascorbic acid) resulted in a strong trend towards reduction in infarct volume. Additional testing of FS (5 mg/kg fluoxetine, 0.5 mg/kg simvastatin) also resulted in a strong trend towards reduction of infarct volume which suggests that ascorbic acid is not an essential part of the drug combination FSA or PSA. While not wishing to be bound by theory, the results in the above examples may translate to the human ischemic stroke population by providing a composition and method for the treatment of neurodegeneration wherein functional recovery is achieved when the drug combination is administered between at least 20-26 hours after ischemic stroke induction and with continued daily administration for at least 31 days.

Having described the invention in detail and by reference to preferred embodiments thereof, it will be apparent that modifications and variations are possible without departing from the scope of the invention.

What is claimed is:

1. A composition comprising: fluoxetine, simvastatin, and ascorbic acid.

2. The composition of claim 1 comprising 0.81 mg/kg to 1.62 mg/kg by weight of said fluoxetine, from 0.081 mg/kg to 0.42 mg/kg by weight of said simvastatin, and 3.24 mg/kg by weight of said ascorbic acid.

* * * * *